United States Patent
Kavoori Sethumadhavan et al.

(10) Patent No.: US 9,638,628 B2
(45) Date of Patent: May 2, 2017

(54) GAS ANALYSIS SYSTEM AND METHOD

(71) Applicant: General Electric Company, Schenectady, NY (US)

(72) Inventors: Nagapriya Kavoori Sethumadhavan, Bangalore (IN); Samhitha Palanganda Poonacha, Jr., Bangalore (IN); David Peter Robinson, Lisburn (GB)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 14/837,200

(22) Filed: Aug. 27, 2015

(65) Prior Publication Data
US 2017/0059476 A1 Mar. 2, 2017

(51) Int. Cl.
*G01N 21/25* (2006.01)
*G01N 21/31* (2006.01)
*G01N 21/27* (2006.01)

(52) U.S. Cl.
CPC ............ *G01N 21/255* (2013.01); *G01N 21/27* (2013.01); *G01N 21/31* (2013.01); *G01N 2201/061* (2013.01); *G01N 2201/068* (2013.01)

(58) Field of Classification Search
CPC ........ G01J 3/26; G01J 3/02; G01J 3/51; G01J 9/00; G01N 21/255
USPC ........................................................ 356/416
See application file for complete search history.

(56) References Cited

U.S. PATENT DOCUMENTS

| 5,801,384 A | 9/1998 | Kirchhevel |
| 6,138,674 A | 10/2000 | Gull et al. |
| 7,423,258 B2 | 9/2008 | DiFoggio |
| 7,907,282 B2 | 3/2011 | Coates |
| 2005/0129577 A1 | 6/2005 | Potapov et al. |
| 2011/0023594 A1* | 2/2011 | Pelletier ............. G01N 21/1702 73/152.18 |
| 2014/0078503 A1* | 3/2014 | Matsushita .......... G02B 26/001 356/416 |
| 2015/0377774 A1* | 12/2015 | Saptari ............... G01N 21/3504 356/70 |

FOREIGN PATENT DOCUMENTS

EP 2287591 A2 2/2011

OTHER PUBLICATIONS

Nogueira, "Development of an Infrared Absorption Spectroscope Based on Linear Variable Filters", Office of Graduate Studies of Texas A&M University, pp. 1-125, Dec. 2006.

(Continued)

*Primary Examiner* — Tarifur Chowdhury
*Assistant Examiner* — Md M Rahman
(74) *Attorney, Agent, or Firm* — Nitin N. Joshi

(57) ABSTRACT

A gas analysis system and method filter different wavelengths of incident light using a variable light filter at different locations along a length of the variable light filter to form filtered light. The variable light filter is configured to be disposed between a light source generating plural different wavelengths of the incident light and a gas sample. Intensities of wavelengths of the filtered light are determined after the incident light generated by the light source passes through the variable light filter and the gas sample. The gas sample may be identified from among different potential gasses based on the intensity of the one or more wavelengths of the filtered light that is determined by the light detector.

19 Claims, 6 Drawing Sheets

(56) References Cited

OTHER PUBLICATIONS

Voorderhake, "Micro spectrometer for the measurement of the composition of new gas", TUDelft, pp. 1-144, Sep. 11, 2011.
Rohwedder et al., "iHWG-µNIR: a miniaturised near-infrared gas sensor based on substrate-integrated hollow waveguides coupled to a micro-NIR-spectrophotometer", Analyst, May 12, 2014.
Abatzi, "Spectral deconvolution and concentration mapping in complex biochemical stains", Technical University of Crete, Greece School of Electronic and Computer Engineering, pp. 1-125, Jul. 2014.

* cited by examiner

GAS ANALYSIS SYSTEM AND METHOD

FIELD

Embodiments of the subject matter described herein relate to identifying a gas in a sample using light.

BACKGROUND

Various systems identify gases using laser light. Some systems include laser light sources that each emits a single wavelength of light. The single wavelength light passes through a sample of the unidentified gas, and the intensity of the single wavelength light is measured. Multiple different lasers can be used to determine the intensities of multiple different wavelengths of light at different times. The intensities can reveal the identity of the gas.

One problem with these types of laser-based systems is the cost and complexity. In order to identify a variety of gases, many different lasers may be needed, which can be expensive and increase the complexity in design and alignment of the systems.

Other systems use a light source that generates many wavelengths of light or a continuum of wavelengths and a filter wheel having many different filters. The different filters selectively transmit (or pass) different wavelengths of light and block other wavelengths from the light generated by the light source. The filter wheel is rotated in a batch manner to move different filters between the light source and the gas at different times. The intensities of the lights passing through the gas are examined to identify the gas.

One problem with both the laser and filter wheel approaches is that these techniques may require some prior knowledge of the gases that are present in a sample. The presence of additional gases can change a baseline of the measured intensities or add to the data and hamper the determination of the gas composition and gas concentrations in the sample. Another approach uses Fourier transform infrared spectroscopy (FTIR) to examine the gas, but this approach is costly, complex, and generally not deployable outside of a laboratory setting.

SUMMARY

In one embodiment, a gas analysis system includes a linear variable light filter configured to filter different wavelengths of incident light at different locations along a length of the variable light filter to form filtered light. The variable light filter is configured to be disposed between a light source generating plural different wavelengths of the incident light and a gas sample. The system also includes a light detector configured to determine an intensity of one or more wavelengths of the filtered light after the incident light generated by the light source passes through the variable light filter and the gas sample. The light detector also is configured to identify the gas sample from among different potential gasses based on the intensity of the one or more wavelengths of the filtered light that is determined by the light detector.

In one aspect, the resolution problem of previous systems is overcome by moving the detector relative to the filter and/or sample, moving the filter relative to the detector and/or sample, and/or moving the light source relative to the filter, detector, and/or sample. Moving one or more of the filter, detector, and/or light source can allow for the detector to measure more wavelengths of light using a broadband light source as the light source, without requiring many different single-wavelength lights (e.g., lasers). Optionally, the light may be chopped by alternating between allowing light to propagate through the sample and blocking the light from propagating through the sample. This chopping can cause pressure waves to form in the sample, which can then be detected by the detector (e.g., acoustic detection) in order to identify the gases in the sample.

In one embodiment, a gas analysis method includes receiving incident light having plural different wavelengths of light at a variable light filter, filtering different wavelengths of the incident light at different locations along a length of the variable light filter to form filtered light, passing one or more of the incident light or the filtered light through a gas sample, determining an intensity of one or more wavelengths of the filtered light after the incident light generated by the light source passes through the variable light filter and the gas sample, and identifying the gas sample from among different potential gasses based on the intensity of the one or more wavelengths of the filtered light that is determined.

In one embodiment, a gas analysis system includes a variable light filter configured to filter different wavelengths of incident light at different locations in the variable light filter to form filtered light. The variable light filter is configured to be disposed between a light source generating plural different wavelengths of the incident light and a gas sample. The system also includes a light detector configured to determine an intensity of one or more wavelengths of the filtered light after the incident light generated by the light source passes through the variable light filter and the gas sample. The light detector also is configured to identify the gas sample from among different potential gasses based on the intensity of the one or more wavelengths of the filtered light that is determined by the light detector. The system further includes a chopping device configured to prevent the incident light generated by the light source from reaching the variable light filter during first time periods and to allow the incident light generated by the light source to reach the variable light filter during different, second time periods, wherein the first and second time periods are interleaved with each other with respect to time.

DETAILED DESCRIPTION

Figure 1:
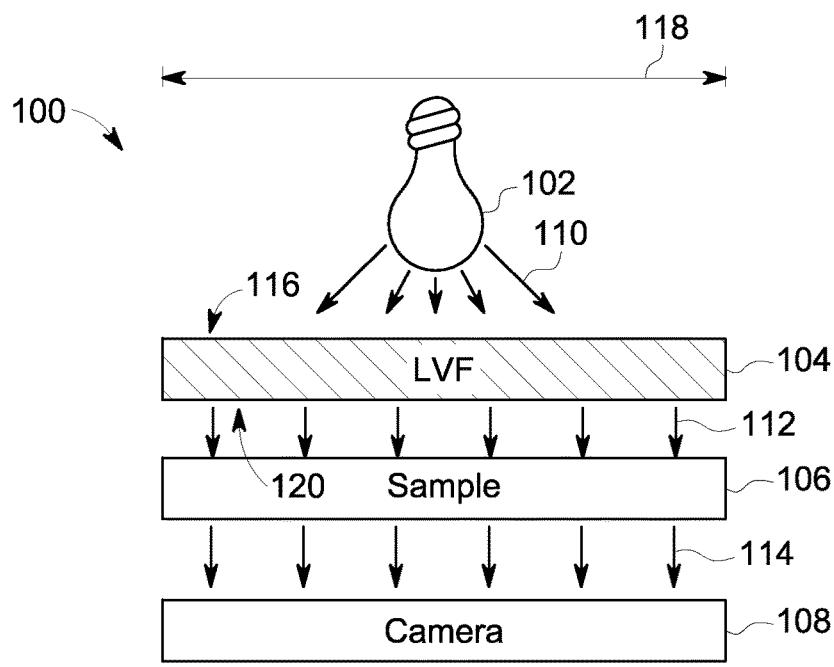
FIG. 1 illustrates one embodiment of a gas analysis system.

FIG. 1 illustrates one embodiment of a gas analysis system 100. The system 100 includes a light source 102 ("BB Source" in FIG. 1) that generates many different wavelengths of incident light 110. The light source 102 may be a broadband light source that generates white light, light with a spectrum of wavelengths of light 102 that includes all wavelengths of light, light with a spectrum of wavelengths of light 102 including all wavelengths of light sought to be examined (e.g., by passing through a gas sample), etc. In one embodiment, the light source 102 is not a laser light source that generates a single wavelength of light and does not include multiple laser light sources each generating a single wavelength of light. In one aspect, the light source 102 generates the many different wavelengths of light 110 at the same time.

The system 100 also includes a linear variable light filter 104 ("LVF" in FIG. 1). The light filter 104 filters different wavelengths of light at different locations along a length dimension 118 of the light filter 104. In the illustrated embodiment, incident light 110 is received on an incident side 116 of the light filter 104, different wavelengths of the light 110 are filtered at different locations along the length dimension 118 of the light filter 104, and filtered light 112 exits the light filter 104 through a filtered side 120 of the light filter 104.

Figure 2:
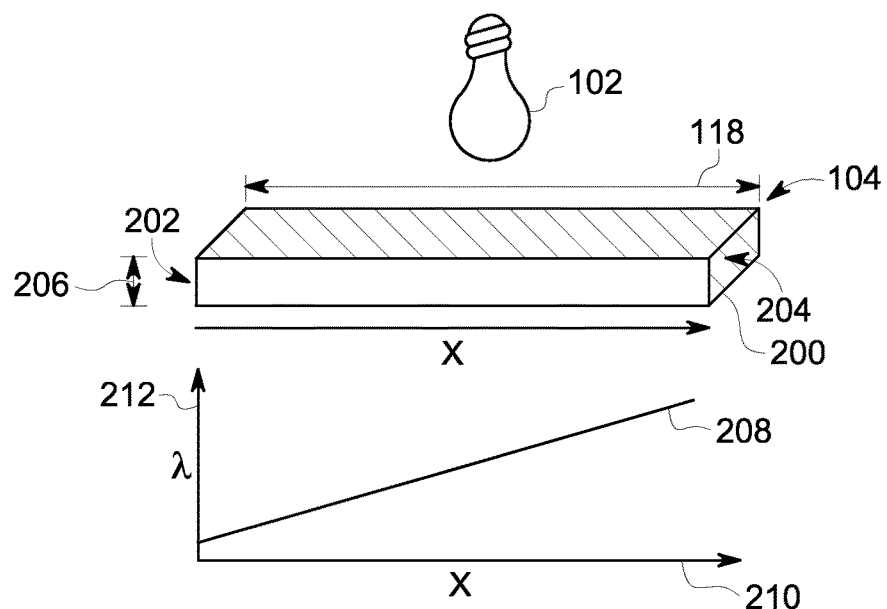
FIG. 2 illustrates operation of a linear variable light filter shown in FIG. 1 according to one example.

FIG. 2 illustrates operation of the linear variable light filter 104 shown in FIG. 1 according to one example. The light filter 104 is a light transmissive, elongated body 200 extending between opposite ends 202, 204 and the sides 116, 120. The length dimension 118 of the light filter 104 is measured from one end 202 or 204 to the opposite end 204 or 202, and thickness dimensions 206 of the light filter 104 are measured from one side 116 or 120 to the opposite side 120 or 116. The thickness dimension 206 of the light filter 104 can vary as a function of distance x along the length dimension 118 of the light filter 104.

The light filter 104 filters different wavelengths of light as a function of distance x along the length dimension 118 of the light filter 104. A filter relationship 208 is shown in FIG. 2 along a horizontal axis 210 representative of distance x along the length dimension 118 of the light filter 104 from the end 202 to the end 204 of the light filter 104. The filter relationship 208 also is shown alongside a vertical axis 212 representative of wavelengths of light that are able to pass through the light filter 104 at the different distances x along the length dimension 118 of the light filter 104. The light passing through the light filter 104 (referred to as filtered light) is spatially wavelength filtered light. As one example, a 2.5 micrometer to 5 micrometer linear variable filter 104 would output a filtered light having a 2.5 micrometer wavelength at one end 202 and a 5 micrometer wavelength light at the other end 204. Different wavelengths of light may be filtered by the light filter 104 at different locations along the length of the filter 104. For example, at a location that is one millimeter away from the end 202, the filter 104 may prevent wavelengths of light other than wavelengths of 2.51 micrometers from passing through the filter 104. At a location that is two millimeters away from the end 202, the filter 104 may prevent wavelengths of light other than wavelengths of 2.52 micrometers from passing through the filter 104. At a location that is three millimeters away from the end 202, the filter 104 may prevent wavelengths of light other than wavelengths of 2.53 micrometers from passing through the filter 104, and so on. The filter 104 may be a continuous body such all of the filter 104 allows at least some light to pass through, and no part of the filter 104 between the end 202 and the end 204 blocks all light from passing through.

Returning to the description of the system 100 shown in FIG. 1, the light exiting the filtered side 120 of the light filter 104 is filtered light 112. The filtered light 112 has different wavelengths of light at different locations along the length dimension 118 of the light filter 104. The filtered light 112 passes through a gas sample 106 ("Sample" in FIG. 1), which can include a light transmissive container holding one or more gases inside. Different wavelengths of the filtered light 112 can be absorbed or pass through the gases inside the gas sample 106 and exit the gas sample 106 as representative light 114. The wavelengths of the representative light 114 can represent the gas or gases in the sample 106.

A light detector 108 ("Camera" in FIG. 1) receives the representative light 114 exiting from the gas sample 106. The light detector 108 can include or represent a spectrometer that measures intensities of the different wavelengths of the light 114. Because different gases can absorb different wavelengths of light 112 by different amounts, the intensities of the several wavelengths of the light 114 that are received and measured by the light detector 108 can indicate the gas or gases in the sample 108. In one aspect, the light detector 108 can include and/or be connected with hardware circuitry that includes and/or is connected with one or more processors. The processors can examine the intensities and/or acoustic waves (as described below) to identify the gas, combination of gases, and/or gas concentrations in the sample 106, as described below.

Figure 3:
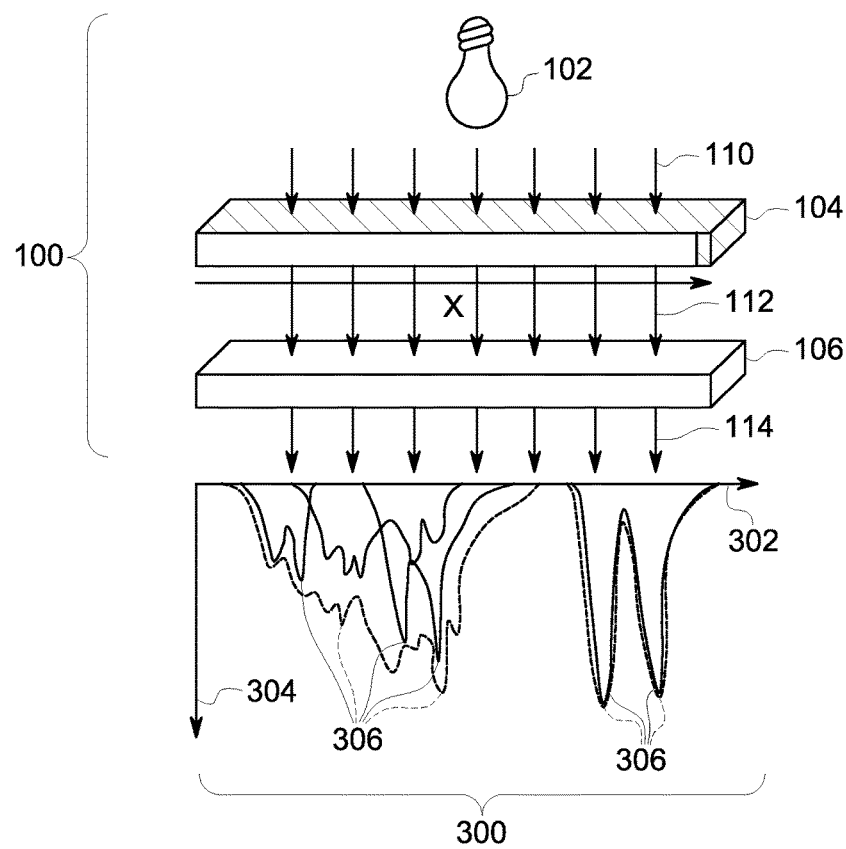
FIG. 3 illustrates one embodiment of the system shown in FIG. 1 generating a spectrum of the wavelengths of light exiting from a gas sample shown in FIG. 1.

FIG. 3 illustrates one embodiment of the system 100 shown in FIG. 1 generating a spectrum 300 of the wavelengths of the light 114 exiting from the gas sample 106. The spectrum 300 is shown alongside a horizontal axis 302 representative of distance x along the length dimension 118 of the light filter 104 and a vertical axis 304 representative of intensities of the wavelengths of the light 114 detected by the light detector 108 (not shown in FIG. 3) at the different locations along the light filter 104. Optionally, because the light filter 104 filters the wavelengths of the light 112, 114 as a function of distance x, the horizontal axis 302 optionally may represent different wavelengths of the light 114.

Different gases, combinations of gases, and/or different concentrations of gases in the sample 106 can produce different spectra 300. Some gases, combinations, and/or concentrations have peaks 306 in the spectra 300 at different wavelengths or distances along the horizontal axis 302. The locations, presence, and/or absence of the peaks 306 can indicate which gases, combinations of gases, and/or gas concentrations are in the sample 106. The detector 108 can compare the spectrum 300 obtained from a gas sample 106 to previously acquired or determined spectra that are associated with different gases, gas combinations, and/or gas concentrations. Depending on which of the previously acquired or determined spectra or spectrum that the spectrum 300 matches (or more closely matches than one or more other spectra or spectrum) based on the peaks 306, the detector 108 can identify the gas, gas combination, and/or gas concentration in the sample 106. For example, certain gases, combinations of gases, and/or gas concentrations absorb some wavelengths of light more than other wavelengths of light. Knowing which wavelengths of light are and/or are not absorbed by certain gases, gas combinations, and/or gas concentrations, the detector 108 can compare the peaks 306 in the spectrum 300 to determine how well the gas in the sample 106 absorbs the different wavelengths of light. Based on this information, the detector 108 can identify the gas, gas combinations, and/or gas concentrations in the sample 106.

In the embodiment shown in FIG. 1, the light filter 104 is disposed between the sample 106 and the light source 102, and the sample 106 is disposed between the light filter 104 and the detector 108. Alternatively, the light filter 104 and/or sample 106 may be in another location.

Figure 4:
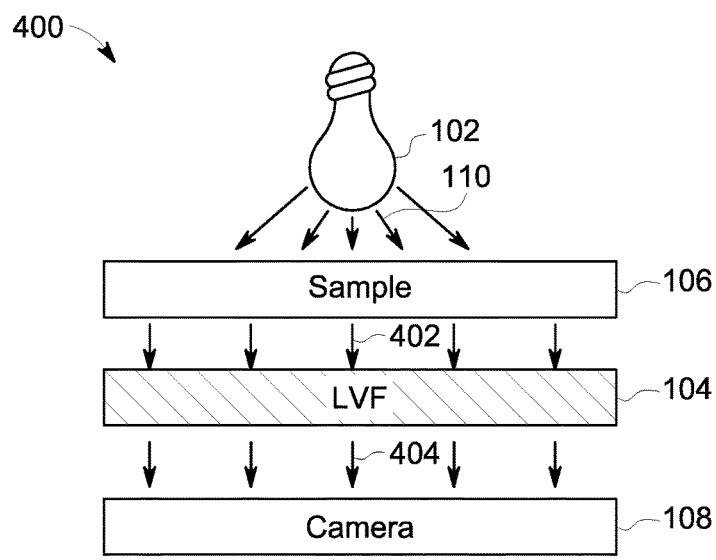
FIG. 4 illustrates another example of a gas analysis system.

FIG. 4 illustrates another example of a gas analysis system 400. The system 400 can include the same components as the system 100 shown in FIG. 1, but in different locations. The system 400 includes the sample 106 between the light source 102 and the light filter 104, and the light filter 104 between the sample 106 and the detector 108. In operation, the light source 102 generates the incident light 110 having many different wavelengths of light. Instead of the light 110 being filtered before passing through the sample 106, the light 110 passes through the sample 106. Different gases absorb different wavelengths of the light 110 in different amounts, so representative light 402 that exits the sample 106 represents the gas or gases in the sample 106.

The representative light 402 can include many different wavelengths of light at the same location. In order to separate the different wavelengths of light 402 from each other, the representative light 402 then passes through the light filter 104. As described above, different locations along the length of the light filter 104 remove different wavelengths of the light 402, so a filtered light 404 having different wavelengths of light at different locations along the length of the light filter 104 exits from the light filter 104.

The filtered light 404 has passed through the sample 106 so that different wavelengths of the light 404 were absorbed by the gas or gases in the sample 106 and has passed through the light filter 104 so that the light 404 has different wavelengths at different locations. As a result, the detector 108 can receive the light 404, measure intensities of the light 404 at the different locations, and identify the gas, gas combinations, and/or gas concentrations in the sample 106.

Figure 5:
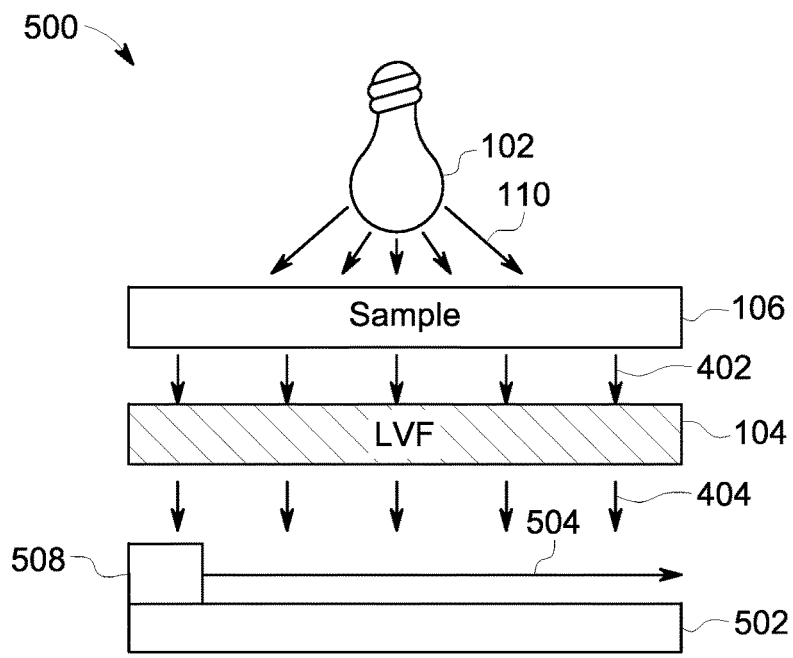
FIG. 5 illustrates another example of a gas analysis system.

FIG. 5 illustrates another example of a gas analysis system 500. The system 500 can include at least some of the same components as the systems 100, 400 shown in FIGS. 1 and 4, but with a detector 508 that moves relative to the light filter 104 and/or sample 106. Similar to the system 400, the system 500 includes the sample 106 between the light source 102 and the light filter 104, and the light filter 104 between the sample 106 and the detector 108. Alternatively, however, the system 500 may include the filter 104 between the light source 102 and the sample 106 and the sample 106 between the filter 104 and the detector 508.

The detector 508 is operatively connected with an actuator 502 that moves the detector 508 along a direction of travel 504. Optionally, the actuator 502 also may move the detector 508 in an opposite direction. The actuator 502 can include one or more belts, chains, gears, or the like, that move the detector 508 so that the detector 508 receives different portions of the light 404 exiting the filter 104 (or the light 114 exiting the sample 106, depending on which of the filter 104 or sample 106 is closer to the detector 508). The detectors 108 in the systems 100, 400 may detect many more wavelengths of the light 114, 404 that is filtered by the filter 104 and passes through the sample 106 than the detector 508. The detector 508 may be smaller than the detector 108 such that the detector 508, when stationary, detects fewer wavelengths of light than the detector 108. The actuator 502 can move the detector 508 so that the detector 508 sweeps below the filter 104 and sample 106 to detect many more wavelengths of light, such as the same amount of wavelengths of light as the detector 108 shown in FIGS. 1 and 4.

Alternatively, the light filter 104 may be moved relative to the detector 508. For example, the light filter 104 may be moved along one or more directions relative to the detector 508 (e.g., along a direction that is parallel to the direction 504 and/or in an opposite direction) to filter different portions of the light 402 at different times. The detector 508 may be stationary, or also may move (e.g., both the filter 104 and the detector 508 may move together beneath the sample 106). In such an embodiment, the actuator 502 can be connected with the filter 104 to move the filter 104 relative to the detector 508 and/or one actuator 502 may be connected with the filter 104 and another actuator 502 can be connected with the detector 508 to move both the filter 104 and the detector 508 (e.g., by concurrently or simultaneously moving the filter 104 and detector 508 in different directions).

Figure 6:
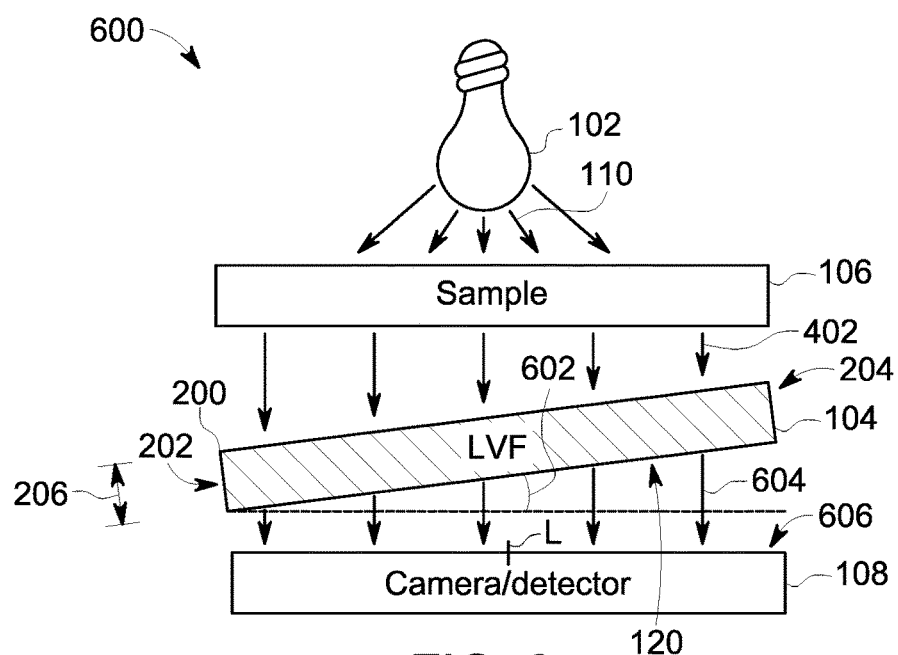
FIG. 6 illustrates another example of a gas analysis system.

FIG. 6 illustrates another example of a gas analysis system 600. The system 600 can include at least some of the same components as the systems 100, 400, 500 shown in FIGS. 1, 4, and 5, but with the light filter 104 disposed at an angle 602, such as an acute angle or another angle. The light filter 104 shown in FIGS. 1, 4, and 5 is oriented parallel or approximately parallel to the sample 106 and the detector 108 ("Camera/detector" in FIG. 6). For example, the surface of the sample 106 that faces the opposing side of the light filter 104 and that same side of the light filter 104 are parallel to each other, and/or the surface of the detector 108 that faces the opposing side of the light filter 104 and that same side of the light filter 104 are parallel to each other.

In contrast, the light filter 104 is angled with respect to the detector 108 and the sample 106 in FIG. 6. The body 200 of the light filter 104 may have different thickness dimensions 206 along the length of the body 200 from the end 202 to the end 204. For example, the thickness dimension 206 of the body 200 of the light filter 104 may change as a function of distance x along the length of the body 200. This thickness dimension 206 may change to allow for different wavelengths of light to pass through the light filter 104 at different distances x while filtering out (e.g., blocking) other wavelengths of light from passing through the filter 104 at the same distances x.

But, the varying thickness dimension 206 also can cause filtered and representative light 604 (e.g., light that has passed through the sample 106 and that has been filtered by the filter 104) exiting from the filter 104 to be refracted. This refraction can cause at least some wavelengths of the light to be received in different locations at the detector 108. For example, the detector 108 may attempt to measure certain wavelengths of the light passing through the filter 104 and the sample 106 at different locations. The refraction of light caused by the filter 104 may direct some wavelengths of light to other locations. For example, if the detector 108 is measuring a wavelength $\lambda$ of light at a location L, the refraction of the light having the wavelength $\lambda$ caused by the filter 104 may cause the light having the wavelength $\lambda$ to be received at the detector 108 at a location (L+$\Delta$L) or (L+$\Delta$L), where $\Delta$L represents the spatial shift in the direction of travel of the light having the wavelength $\lambda$ caused by the diffraction. Light of other wavelengths also may be spatially shifted with respect to the detector 108 due to diffraction caused by the filter 104.

In order to compensate for this spatial shift in the direction of travel of the light directed toward the detector 108, the light filter 104 may be oriented at the angle 602 with respect to the detector 108. If the sample 106 is disposed between the light filter 104 and the detector 108, then the filter 104 may be disposed at the angle 602 with respect to the sample 106. This angle 602 can represent the angle between a plane defined by or coextensive with the filtered side 120 of the filter 104 and a plane defined by or coextensive with a receiving side 606 of the detector 108. The receiving side 606 can be the part of the detector 108 through which the light 604 is received for measurement.

The angle 602 at which the filter 104 is inclined may be based on the thickness dimensions 206 of the filter 104. For example, for larger thickness dimensions 206 and/or larger changes in the thickness dimensions 206 (e.g., between the end 202 and the end 204 of the filter 104), more refraction of the light 402 may occur and the angle 602 may need to be larger than for smaller thickness dimensions 206 and/or smaller changes in the thickness dimensions 206.

Figure 7:
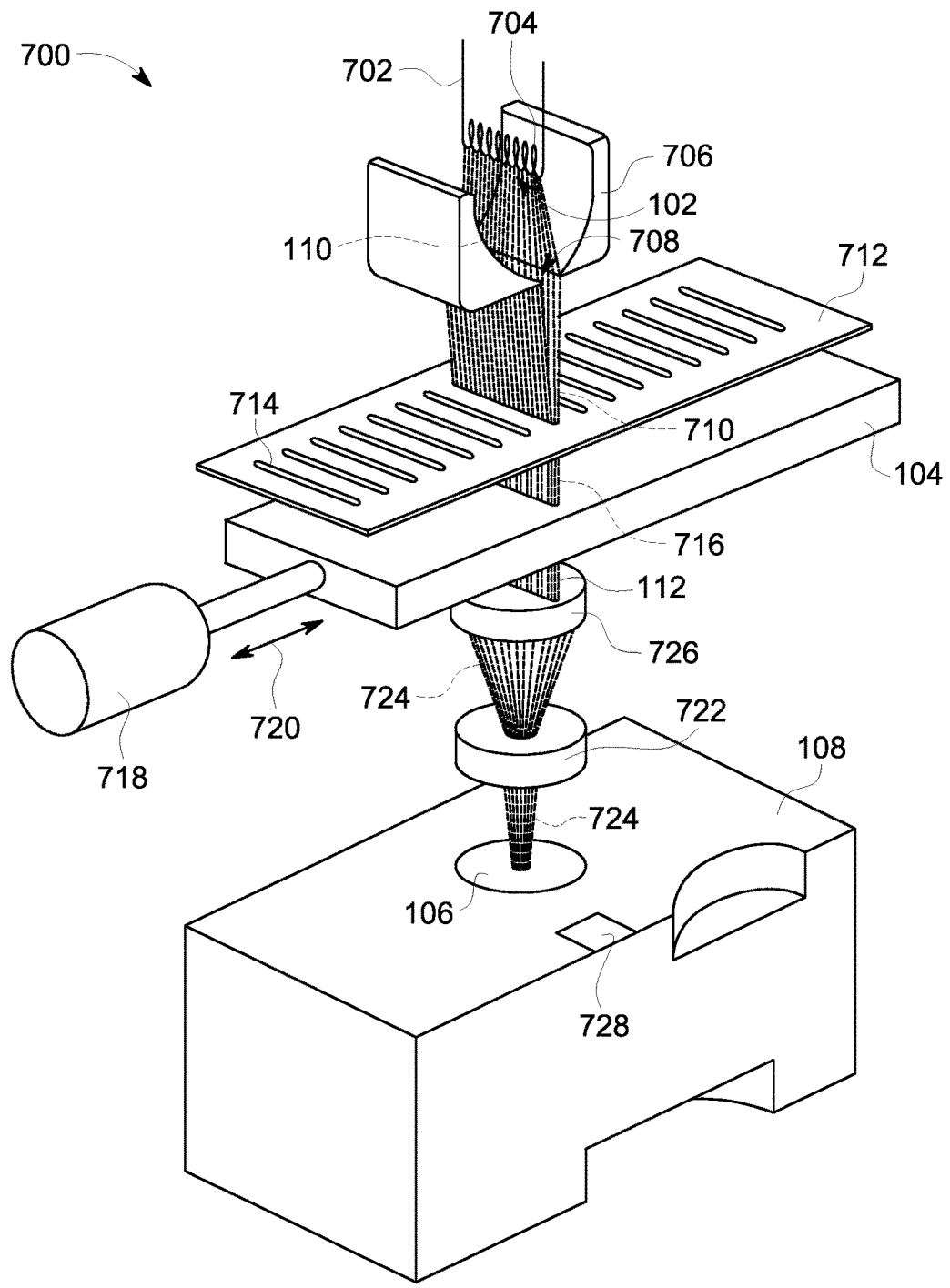
FIG. 7 illustrates another example of a gas analysis system.

FIG. 7 illustrates another example of a gas analysis system 700. The system 700 can include at least some of the same components as the systems 100, 400, 500, 600 shown in FIGS. 1, 4, 5, and 6. The system 700 includes the light source 102, which is illustrated as one or more filaments 702 wrapped around a black body 704. The system 700 also includes the light filter 104, the gas sample 106, and the detector 108. In the illustrated embodiment, the light filter 104 is between the light source 102 and the sample 106, and the sample 106 is between the light filter 104 and the detector 108. Alternatively, one or more other arrangements of these components may be used, as described herein.

The light source 102 generates the light 110, which is collimated by a slit concentrator 706. The slit concentrator 706 represents a body that reflects or blocks some of the light 110 from passing there through to the filter 104 and sample 106. The slit concentrator 706 includes one or more collimating slots 708 that allow at least some of the light 110 to pass through. The light 110 that passes through the slit concentrator 706 is referred to as collimated light 710. The slit concentrator 706 may increase the intensity of the light passing there through relative to a system that does not include the slit concentrator 706. Alternatively, the slit concentrator 706 may not be included in the system 700.

In the illustrated embodiment, a chopping device 712 is disposed between the light source 102 and the light filter 104, and between the slit concentrator 706 and the light filter 104. The chopping device 712 may be connected (e.g., mechanically coupled by one or more adhesives or connectors) with the light filter 104, with the chopping device 712 and filter 104 being shown in an exploded view in FIG. 7. Alternatively, the chopping device 712 may be detached or separated from the light filter 104. If the slit concentrator 706 is not included in the system 700, then the chopping device 712 may be disposed between the light source 102 and the light filter 104. The chopping device 712 includes a mask body having openings 714, such as slits, disposed therein. The body of the chopping device 712 blocks passage of the light 110, 710 through the chopping device 712 to the filter 104 and gas sample 106. The openings 714 extend through the body of the chopping device 712 and allow the light 110, 710 to pass through the chopping device 712 to the filter 104 and gas sample 106. In one aspect, the openings 714 may be elongated slots or slits that are elongated in directions that are parallel to a direction along which the slot or slots 708 of the concentrator 706 are elongated. The light 110, 710 passing through an opening 714 may be referred to as chopped light 716.

The filter 104 may be operably connected with an actuation assembly 718 that moves the filter 104 relative to the sample 106. Optionally, the chopping device 712 may be connected with the actuation assembly 718 or another actuation assembly for moving the chopping device 712. For example, the chopping device 712 may lie on or be connected with the filter 104, similar to a mask. Alternatively, the chopping device 712 may be separate from the filter 104. The actuation assembly 718 can represent one or more shafts, pistons, solenoids, motors, gears, or the like, that move the filter 104 back and forth along opposite directions 720. The chopping device 712 can be used to control heating and cooling of the gas or gases in the sample 106, which can generate pressure waves within the sample 106 that can be used to acoustically determine concentrations of one or more gases in the sample 106, as described below.

The light exiting the filter 104 can propagate through one or more lenses 722, 726 and exit the one or more lenses 722, 726 as focused light 724. The lenses 722, 726 can focus the light 724 toward sample 106, which may be connected with or inside the detector 108, as shown in FIG. 7. The detector 108 measures intensities of the focused light 724, which can be used to identify the gas, combination of gases, and/or gas concentrations in the sample 106, as described above.

Figure 8:
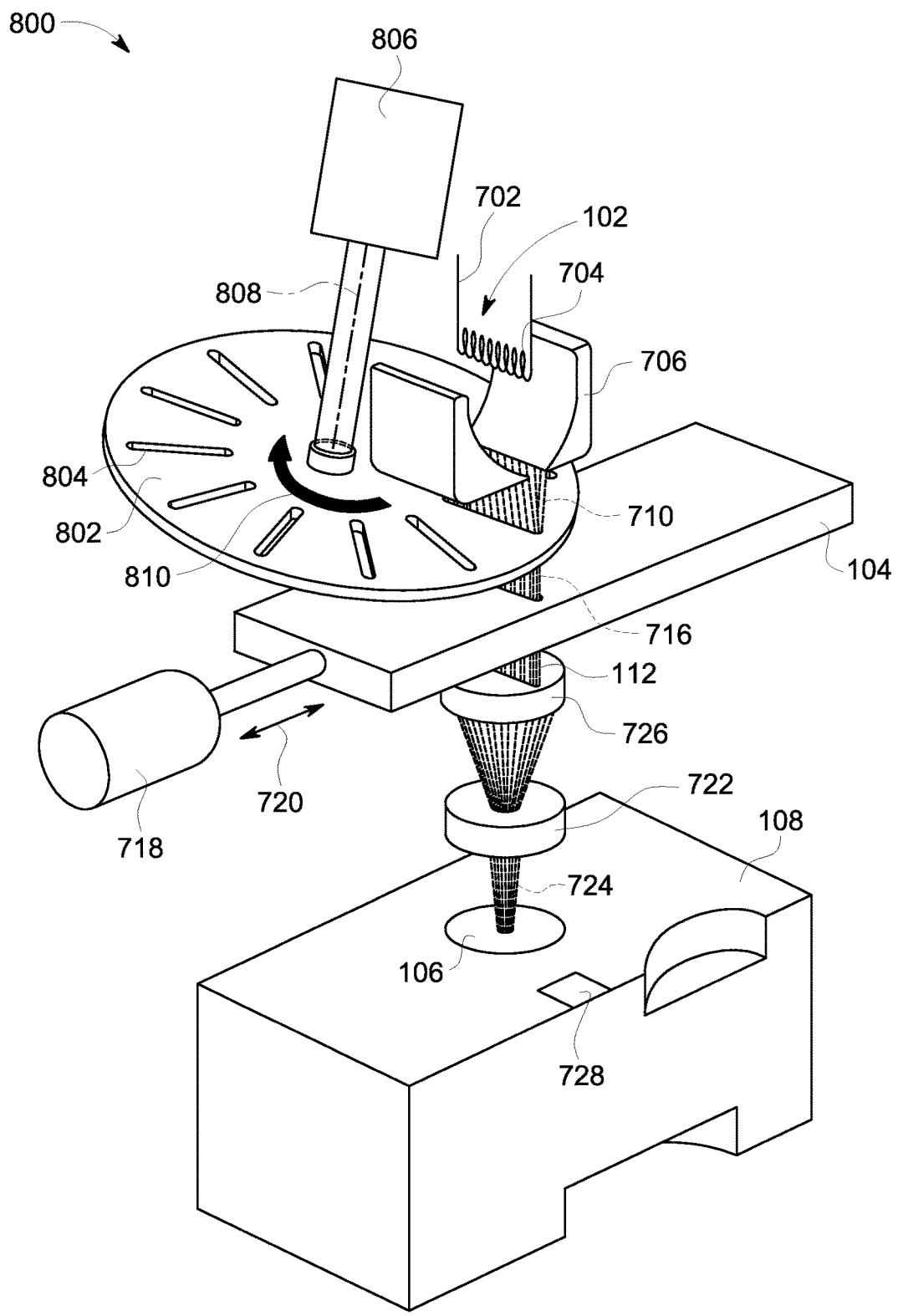
FIG. 8 illustrates another example of a gas analysis system.

FIG. 8 illustrates another example of a gas analysis system 800. The system 800 can include at least some of the same components as the systems 100, 400, 500, 600, 700 shown in FIGS. 1, 4, 5, 6, and 7. The system 800 includes the light source 102, the light filter 104, the gas sample 106, the detector 108, the concentrator 706, the lenses 722, 726, and the actuator 718, as described above. The system 800 also includes a chopping device 802 disposed between the light source 102 and the light filter 104, and between the slit concentrator 706 and the light filter 104. If the slit concentrator 706 is not included in the system 800, then the chopping device 802 may be disposed between the light source 102 and the light filter 104.

The chopping device 802 includes a mask body having openings 804, such as slits, disposed therein. The body of the chopping device 802 blocks passage of the light 110, 710 through the chopping device 802 to the filter 104 and gas sample 106. The openings 804 extend through the body of the chopping device 802 and allow the light 110, 710 to pass through the chopping device 802 to the filter 104 and gas sample 106. In one aspect, the openings 804 may be elongated slots or slits. As described above, the light 110, 710 passing through an opening 804 may be referred to as chopped light 716.

The chopping device 802 may be operably connected with an actuation assembly 806 that rotates the chopping device 802 relative to the sample 106 and filter 104. The actuation assembly 806 can represent one or more shafts, pistons, solenoids, motors, gears, or the like, that are connected with the chopping device 802 by one or more shafts 808 or other bodies to rotate the chopping device 802 along a rotary direction 810.

Rotating the chopping device 802 causes the sample 106 to be exposed to light during first time periods and be blocked from the light during different, second time periods. The first time periods occur when the slot 708 in the concentrator 706 and an opening 804 of the chopping device 802 are aligned with each other in a direction that linearly extends from the light source 102 to the gas sample 106. The second time periods occur when an opening 804 of the chopping device 802 is not aligned with the slot 708 and light source 102. For example, the second time periods can occur when sections of the chopping device 802 that are between the openings 802 block passage of light.

Figure 9:
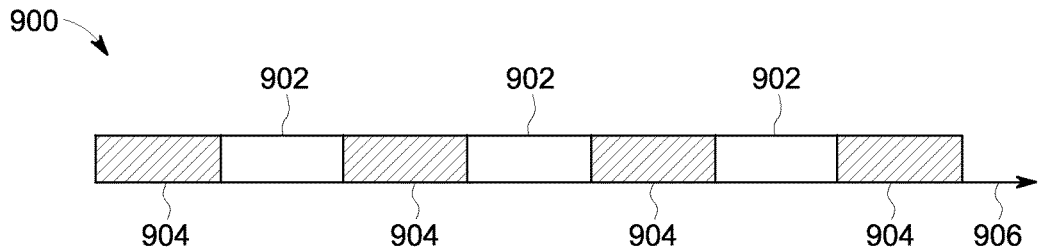
FIG. 9 illustrates a timing diagram for controlling a temperature of the gas or gases in the sample according to one example.

FIG. 9 illustrates a timing diagram 900 for controlling a temperature of the gas or gases in the sample 106 according to one example. The timing diagram 900 illustrates several first time periods 902 interleaved with several second time periods 904 shown alongside a horizontal axis 906 representative of time. The first time periods 902 and the second time periods 904 may be interleaved with each other such that each first time period 902 is separated from the preceding first time period 902 by a second time period 904 and is separated from the next first time period 902 by another second time period 904. The first time periods 902 and the second time periods 904 may be interleaved with each other such that each second time period 904 is separated from the preceding second time period 904 by a first time period 902 and is separated from the next second time period 904 by another first time period 902. The number of first time periods 902 and second time periods 904 shown in FIG. 9 is one example and should not be interpreted as limiting on all embodiments disclosed herein. The first and second time periods 902, 904 are shown as having equivalent durations, but the first time periods 902 may be longer or shorter than the second time periods 904.

Returning to the description of the system 800 shown in FIG. 8, the first time periods 902 shown in FIG. 9 can represent the time periods that the light generated by the light source 102 passes through the slot 708 in the concentrator 706, through an opening 804 in the chopping device 802, through the filter 104, and into the sample 106. The second time periods 904 shown in FIG. 9 can represent the time periods that the light generated by the light source 102 passes through the slot 708 in the concentrator 706, but is blocked from reaching the sample 106 by a segment of the chopping device 802 that extends between the openings 804. Controlling the size of the openings 804, the size of the chopping device 802 extending between the openings 714, and/or how rapidly the chopping device 802 is rotated can control how much the gas or gases in the sample 106 are heated. The movement of the chopping device 802 can keep the heat transferred into and stored in the gas or gases of the sample 106 low enough to prevent the amount of light absorbed by the gas or gases from significantly changing. Optionally, the chopping device 802 can be used to control heating and cooling of the gas or gases in the sample 106, which can generate pressure waves within the sample 106 that can be used to acoustically determine concentrations of one or more gases in the sample 106, as described below.

The light 716 that passes through an opening 804 in the chopping device 802 is filtered by the filter 104 and can propagate through one or more lenses 722, 726 and exit the one or more lenses 722, 726 as focused light 724. The lenses 722, 726 can focus the light 724 toward sample 106, which may be connected with or inside the detector 108, as shown in FIG. 9. The detector 108 measures intensities of the focused light 724, which can be used to identify the gas, combination of gases, and/or gas concentrations in the sample 106, as described above.

As described above, the chopping devices 712, 802 can be used to control when the gas sample 106 is exposed to light (and thereby heated) and when the gas sample 106 is not exposed to light (and thereby cooled). With respect to the chopping device 712 shown in FIG. 7, the chopping device 712 may be connected with the filter 104 such that movement of the filter 104 and chopping device 712 can cause the sample 106 to be exposed to light during first time periods (e.g., the time periods 902 shown in FIG. 9) and blocked form the light during second time periods (e.g., the time periods 904 shown in FIG. 9). Similarly, rotation of the chopping device 802 shown in FIG. 8 can cause the sample 106 to be exposed to light during first time periods (e.g., the time periods 902 shown in FIG. 9) and blocked form the light during second time periods (e.g., the time periods 904 shown in FIG. 9).

Alternating between heating and cooling the gas or gases in the sample 106 can cause the gas or gases to alternate between expanding (during heating) and contracting (during cooling). The back-and-forth heating and cooling of the gas or gases in the sample 106 caused by movement of the chopping devices 712, 802 can create acoustic waves in the sample 106. These waves may be created by changes in the pressure of the gas or gases in the sample 106. In one embodiment, the detectors 108 optionally include acoustic pick up devices 728 (shown in FIGS. 7 and 8), such as microphones, that audibly detect the waves created within the sample 106 by the changing temperatures. Alternatively or additionally, the detectors 108 can include temperature-sensitive sensors (e.g., thermocouples, thermometers, etc.) that measure changes in temperature in the gas sample. The changes in temperature can be synchronously demodulated at a chopping frequency. The chopping frequency may be the frequency of the waves created in the sample 106. Amplitudes of the measured waves can be determined by the detectors 108 and can represent gas concentrations in the sample. For example, smaller amplitudes of sounds generated by the waves in the sample 106 may be associated with reduced concentrations of gases in the sample 106 relative to larger amplitudes of sounds generated by the waves. The detector 108 can use this information to determine the concentrations of gases within the sample 106.

In one embodiment, the signal collected at the detector is analyzed using programs to decouple spectral contributions from each gas present in the sample. The individual concentrations of gases can be determined from prior knowledge of the gas spectra. For example, previous spectra of wavelengths of the light can be determined for samples having known gas constituents and concentrations. The previously obtained spectra can be compared to spectra obtained from gas samples under examination having unknown gas constituents and/or concentrations in order to determine the makeup and concentrations of the gases in the samples under examination.

In one aspect, a sum of spectra can be determined as a linear combination of individual gas spectra. Decomposition can be performed by various methods including, but not limited to, least squares error minimization, principal component analysis, etc. To account for those gases that are not part of the original set used for characterization (e.g., the spectra generated from known gas samples), the residual signal can be traced as a function of time to improve prediction accuracy. The evolution rate of the residuals can be tied to the presence of trace proportions of unmeasured gas, as this rate would be different from the rate of change of other faster noise-related sources. The rate of change in concentrations of other measurable gas components (e.g., the gas components that were in both the previous spectra generated from known gas samples and in the spectra generated for the gas sample under examination) can be used an indicator of the rate of change of residual trace of uncharacterized gas. For example, the rate of change in concentrations of known gases can be eliminated from the rates of change in other gases (e.g., via use of a tool such as Kalman Filter) can allow for the rate of changes in the other gases to be determined.

Figure 10:
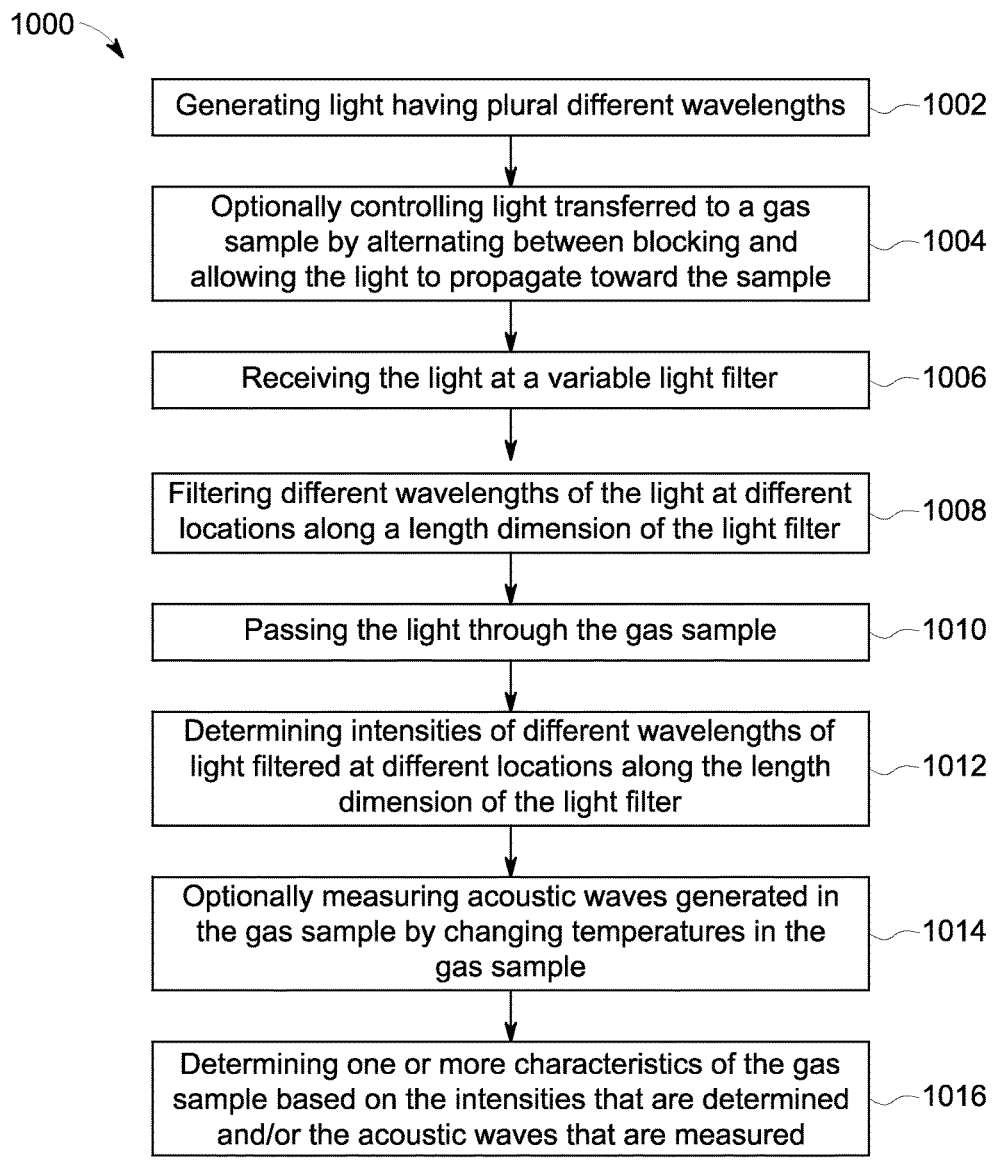
FIG. 10 illustrates a flowchart of one embodiment of a method for analyzing a gas sample.

FIG. 10 illustrates a flowchart of one embodiment of a method 1000 for analyzing a gas sample. The method 1000 may be performed by one or more embodiments of the gas analysis systems described herein. In one embodiment, the method 1000 represents one or more operations, steps, or processes of an algorithm that can be used to program or direct the one or more processors included in and/or connected with the detector 108 in order to identify gases, combinations of gases, and/or gas concentrations in gas samples 106.

At 1002, light having different wavelengths is generated. At 1004, light propagating through a gas sample is optionally controlled by alternating between blocking the light from reaching the gas sample and allowing the light to reach the gas sample. At 1006, the light is received at a variable light filter. At 1008, different wavelengths of the light are filtered at different locations along a length dimension of the filter. As described above, the filter may filter out different wavelengths of light at different locations along a continuous length of the filter.

At 1010, the light is passed through a gas sample. In one embodiment, the light may be filtered at 1008 prior to passing through the sample at 1010. Alternatively, the light may pass through the sample at 1010 prior to being filtered at 1008.

At 1012, different intensities of different wavelengths of light that is filtered by the light filter and that has passed through the gas sample are determined. The intensities may be measured at different locations along the length dimension of the light filter because only certain wavelengths may pass through the filter at different locations, as described above.

At 1014, acoustic waves generated by the gas sample optionally are measured. These acoustic waves may be created by changing temperatures in the gas sample, which can be caused by alternating between blocking the light and allowing the light to reach the gas sample at 1004. The frequencies and/or amplitudes of the acoustic waves may be measured.

At 1016, one or more characteristics of the gas sample are determined based on the determined intensities of the light and/or the measured acoustic waves. For example, the intensities and/or acoustic waves may be compared with intensities and/or acoustic waves associated with different gases, different gas combinations, and/or gas concentrations. Depending on which intensities and/or acoustic waves match or more closely match the measured intensities and/or acoustic waves than other intensities and/or waves, the identity of one or more gases, gas combinations, and/or gas concentrations may be determined.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose several embodiments of the inventive subject matter and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

What is claimed is:

1. A system comprising:
a variable light filter configured to filter different wavelengths of incident light at different locations along a length of the variable light filter to form filtered light, the variable light filter configured to be disposed between a light source generating plural different wavelengths of the incident light and a gas sample; and
a light detector configured to determine an intensity of one or more wavelengths of the filtered light after the incident light generated by the light source passes through the variable light filter and the gas sample, the light detector also configured to identify the gas sample from among different potential gasses based on the intensity of the one or more wavelengths of the filtered light that is determined by the light detector;

wherein the variable light filter has different thickness dimensions as a function of the length along the variable light filter, the thickness dimensions measured between an incident side of the variable light filter where the incident light is received and a filtered side of the variable light filter where the filtered light leaves the variable light filter, and wherein the variable light filter is configured to be disposed at an angle with respect to the light detector, the angle being based on the different thickness dimensions.

2. The system of claim 1, further comprising a chopping device configured to prevent the incident light generated by the light source from reaching the variable light filter during first time periods and to allow the incident light generated by the light source to reach the variable light filter during different, second time periods, wherein the first and second time periods are interleaved with each other with respect to time.

3. The system of claim 1, further comprising a chopping device having a blocking body configured to block passage of the incident light to the variable light filter, the blocking body having plural collimating openings configured to allow the incident light to pass through the blocking body to the variable light filter, and further comprising an actuator configured to linearly move or rotate the chopping device, relative to the variable light filter.

4. The system of claim 1, further comprising a chopping device having a blocking body configured to block passage of the incident light to the variable light filter, the blocking body having plural collimating openings configured to allow the incident light to pass through the blocking body to the variable light filter, and further comprising an actuator configured to linearly move or rotate the chopping device, relative to the variable light filter to control a temperature of the gas sample.

5. The system of claim 1, wherein the variable light filter is configured to be disposed between the gas sample and the light source such that the incident light generated by the light source is filtered by the variable light filter prior to passing through the gas sample.

6. The system of claim 1, wherein the variable light filter is configured to be disposed between the gas sample and the light detector such that the incident light generated by the light source passes through the gas sample prior to passing through the variable light filter.

7. The system of claim 1, wherein one or more of the light detector is configured to move relative to the variable light filter or the variable light filter is configured to move relative to the light detector such that the light detector determines the intensity of plural different wavelengths of the filtered light as the light detector is at different locations relative to the variable light filter.

8. The system of claim 1, wherein the light detector is configured to determine the intensity of plural different wavelengths of the filtered light after the incident light generated by the light source passes through the variable light filter and the gas sample, the light detector also configured to identify the gas sample from among different potential gasses based on one or more of a spectrum of the intensities or phase response of the plural different wavelengths of the filtered light.

9. The system of claim 1, further comprising a broadband light source configured to generate the incident light.

10. A method comprising:
receiving incident light having plural different wavelengths of light at a variable light filter;
filtering different wavelengths of the incident light at different locations along a length of the variable light filter to form filtered light;
passing one or more of the incident light or the filtered light through a gas sample;
determining an intensity of one or more wavelengths of the filtered light after the incident light generated by the light source passes through the variable light filter and the gas sample; and
identifying the gas sample from among different potential gasses based on one or more of the intensity or phase response of the one or more wavelengths of the filtered light that is determined;
wherein the variable light filter has different thickness dimensions as a function of the length along the variable light filter, the thickness dimensions measured between an incident side of the variable light filter where the incident light is received and a filtered side of the variable light filter where the filtered light leaves the variable light filter, and wherein the variable light filter is configured to be disposed at an angle with respect to the light detector, the angle being based on the different thickness dimensions.

11. The method of claim 10, further comprising preventing the incident light generated by the light source from reaching the variable light filter during first time periods and allowing the incident light generated by the light source to reach the variable light filter during different, second time periods, wherein the first and second time periods are interleaved with each other with respect to time.

12. The method of claim 10, further comprising linearly moving a chopping device having a blocking body configured to block passage of the incident light to the variable light filter and plural collimating openings in the blocking body, the chopping device is moved in a linear or rotated moved to the variable light filter.

13. The method of claim 10, further comprising rotating a chopping device having a blocking body configured to block passage of the incident light to the variable light filter and plural collimating openings in the blocking body, the blocking body linearly moved or rotated relative to the variable light filter.

14. The method of claim 10, wherein filtering the different wavelengths of incident light occurs prior to passing the one or more of the incident light or the filtered light through the gas sample.

15. The method of claim 10, wherein filtering the different wavelengths of incident light occurs after passing the one or more of the incident light or the filtered light through the gas sample.

16. The method of claim 10, further comprising one or more of moving the light detector relative to the variable light filter or moving the variable light filter relative to the light detector such that the light detector determines the intensity of plural different wavelengths of the filtered light as the light detector is at different locations relative to the variable light filter.

17. The method of claim 10, wherein determining the intensity of one or more wavelengths of the filtered light includes determining plural different intensities of plural different wavelengths of the filtered light, and wherein identifying the gas sample includes examining a spectrum of the different intensities of the different wavelengths of the filtered light.

18. The method of claim 10, further comprising generating the incident light using a broadband light source.

19. A system comprising:

a variable light filter configured to filter different wavelengths of incident light at different locations in the variable light filter to form filtered light, the variable light filter configured to be disposed between a light source generating plural different wavelengths of the incident light and a gas sample;

a detector configured to determine an intensity of one or more wavelengths of the filtered light after the incident light generated by the light source passes through the variable light filter and the gas sample, the detector also configured to identify the gas sample from among different potential gasses based on the intensity of the one or more wavelengths of the filtered light that is determined by the detector;

a chopping device configured to prevent the incident light generated by the light source from reaching the variable light filter during first time periods and to allow the incident light generated by the light source to reach the variable light filter during different, second time periods, wherein the first and second time periods are interleaved with each other with respect to time;

wherein the variable light filter has different thickness dimensions as a function of the length along the variable light filter, the thickness dimensions measured between an incident side of the variable light filter where the incident light is received and a filtered side of the variable light filter where the filtered light leaves the variable light filter, and wherein the variable light filter is configured to be disposed at an angle with respect to the light detector, the angle being based on the different thickness dimensions.

* * * * *